United States Patent [19]

Harrison et al.

[11] Patent Number: 5,738,774

[45] Date of Patent: Apr. 14, 1998

[54] EVA CONTAINING ION SELECTIVE MEMBRANES AND METHODS OF MAKING SAME

[75] Inventors: Daniel J. Harrison, Edmonton, Canada; Aaron Neufeld, Upper Peckenham, Australia

[73] Assignee: The Governors of the University of Alberta, Alberta, Canada

[21] Appl. No.: 509,499

[22] Filed: Jul. 28, 1995

[51] Int. Cl.$^6$ .................................................. G01N 27/26
[52] U.S. Cl. ........................................ 204/418; 422/82.03
[58] Field of Search ............................ 204/418; 422/82.03

[56] References Cited

U.S. PATENT DOCUMENTS

| | | | |
|---|---|---|---|
| 3,325,460 | 6/1967 | Schellenberg et al. | 260/87.3 |
| 4,020,830 | 5/1977 | Johnson et al. | 128/2 E |
| 4,214,968 | 7/1980 | Battaglia et al. | 204/195 M |
| 4,454,007 | 6/1984 | Pace | 204/1 T |
| 4,713,165 | 12/1987 | Conover et al. | 204/403 |
| 4,734,184 | 3/1988 | Burleigh et al. | 204/409 |
| 4,770,759 | 9/1988 | Young et al. | 204/418 |
| 4,927,408 | 5/1990 | Haak et al. | 604/20 |
| 4,981,570 | 1/1991 | Yamaguchi et al. | 204/418 |
| 5,055,171 | 10/1991 | Peck | 204/290 R |
| 5,078,856 | 1/1992 | Yamaguchi et al. | 204/418 |
| 5,120,422 | 6/1992 | Liu et al. | 204/416 |
| 5,183,549 | 2/1993 | Joseph et al. | 204/415 |
| 5,401,377 | 3/1995 | Shieh et al. | 204/418 |

FOREIGN PATENT DOCUMENTS

| | | |
|---|---|---|
| 0 339 613 A2 | 11/1989 | European Pat. Off. . |
| 0498572A2 | 1/1992 | European Pat. Off. . |
| 1126613 | 1/1957 | Germany . |

OTHER PUBLICATIONS

PCT International Search Report Jul. 26, 1996.
Br. Polym. J. I. 225 (1969) Elasticisation and Plasticiaation of PNC with Ethylene–vinyl acetate Copolymers.
Kunststoffe 57, 321 (1967) Neuere Entwicklungen auf dem Gebiet der Athylene–Copolymeren.
Anal. Sci. 4, 547, (1988) Neutral Carrier Based Ion–Selective Microelectrodes Design and Application A Review.
Anal. Chim. Acta 255, 35 (1991) Reversible Optical Sensing Membrane for the Determination of Chloride in Serum.
J. Chem. Soc. Far. Trans. 82, 1179 (1986) Design of Anion–Selective Membranes for Clinically Relevant Sensors.
Kunststoffe 1, 1 (1965) Ethylene–Vinyl Acetate Copolymers.
Vsokomol Soved, A15, 1382 (1972) The Effect of Plasticization and Crystallization of Polymers on their Electric Conductivity Ion Mobility and Dipole Sigmental Relaxation.
Vysokomol Soved, A11, 2585 (1969) Structure and Behavior of Copolymers of Ethylene With Polar Monomers.
J. Polym. Sci. A1, 9, 3083 (1971), Structure and Property Relationships in Ethylene–Vinyl Acetate Co–Polymers.
Br. Polym. J. 2, 187 (1970) Ethylene–Vinyl Copolymers for Packaging Applications.
Plaste u. Kautschuk 24, 43 (1977) Ein Neves Prufgerat zur Bestimmung Torsionssteifheit von Plasten in Verbindung mit Einem Festigkeitsprufgerat.
Anal. Chim. Acta 273, 153 (1993), Barium Ion–selective Electrode Based on a New Neutral Carrier Complex.
Talanta 38, 929 (1991) Use of Ethylene–Vinyl–Acetate as a New Membrane Matrix for Calcium Ion–Selective Electrode Preparation.
Material Plastice 25, 177 (1988) Structural Studies on Ion Exchange Membranes Obtained by Functionalization of Polymer Foils.
Clinical Chemistry 32, 1448 (1986) Ion–Selective Membrane Electrodes for Clinical Use.
Kautschuk u. Gummi: Kunststoffe 22, 116 (1969) Levapren–ein Athylen/Vinylacetat–Copolymeriast zm Elastifizeren und Weichmachen von Polyvinylchlorid.

Primary Examiner—Bruce F. Bell
Attorney, Agent, or Firm—Wolf, Greenfield & Sacks, P.C.

[57] ABSTRACT

Ion selective membranes and ion selective electrode constructions which include ethylene vinyl acetate (EVA), a reduced amount of plasticizer and an ion selective material. The ion selective membranes have a low crystallinity. In certain embodiments, the ion selective membranes may further include polyvinyl chloride (PVC), a salt or a combination thereof. The ion selective membrane can be incorporated into an ion selective electrode construction. Methods of manufacturing the ion selective membranes and ion selective electrode constructions are provided.

26 Claims, 1 Drawing Sheet

EVA CONTAINING ION SELECTIVE MEMBRANES AND METHODS OF MAKING SAME

BACKGROUND

1. Field of the Invention

The present invention relates generally to ion selective membranes and more specifically to EVA containing ion selective membranes having low crystallinity and methods of making same.

2. Discussion of the Related Art

Ion selective sensors are commonly used in clinical, analytical and industrial chemical laboratories to provide rapid analysis of the concentration of a variety of analytes in solution. Conventionally, these ion selective sensors include an ion selective membrane which is in contact with the analyte containing solution. The potential difference between a reference electrode placed within the test solution and a contact electrode in communication with the ion selective membrane is used to measure the concentration of the analyte in the test solution.

Ion selective membranes often include a polymeric material, an external plasticizer and an ion sensing component. For example, U.S. Pat. No. 4,214,968 and European Patent No. 0 498 572 A2 disclose such membranes wherein the polymeric material is polyvinyl chloride (PVC). These membranes include at least about twice as much plasticizer as polymer by weight. However, such relatively high amounts of plasticizer can reduce the lifetime of the ion selective sensor due to leaching of the plasticizer into the analyte containing solution.

*Anal. Chim. Acta* 273, 153(1993) and *Talanta* 38, 929 (1991) each disclose ion selective membranes including ethylene vinylacetate copolymer (EVA) and an external plasticizer. The amount of plasticizer within the membrane is nearly triple the amount of EVA within the membrane, so leaching of the plasticizer into the analyte solution can result in a reduced lifetime of these membranes.

Some ion selective membranes have been produced which do not include an external plasticizer. U.S. Pat. Nos. 4,981,570 and 5,078,856 disclose ion selective membranes which comprise PVC and a modified form of EVA. This modified EVA serves as an internal plasticizer and contains oxygen atoms in the backbone of the polymer. However, the introduction of oxygen atoms into the EVA results in membranes which can be both relatively expensive and complex to manufacture.

An ion-exchange membrane containing EVA treated with sulfonic acid is disclosed in *Materiale Plastice* 25, 177 (1988). The acid treatment creates functionalized EVA containing sulfonate groups, and the resulting membranes have increased ion transport within the membrane. However, since these membranes have a relatively small amount of vinyl acetate and are cross-linked, they can be too stiff to be used as ion selective membranes in ion selective sensors.

Thus, existing ion selective membranes often are relatively complex to produce, have relatively short lifetimes or both. Therefore, it remains a challenge in the art to provide ion selective membranes of relatively simple design which contains a relatively low level of materials which can leach into the analyte solution. Accordingly, it is a general purpose of the present invention to provide a membrane capable of having a relatively long lifetime and which is relatively easy to prepare.

SUMMARY OF THE INVENTION

Therefore, it is an object of the present invention to provide an ion selective membrane which includes a relatively low concentration of plasticizer or substantially no plasticizer.

It is another object of the present invention to provide an ion selective membrane in accordance with the preceding object, which is relatively easy to prepare.

It is a further object of the present invention to provide an ion selective membrane in accordance with the preceding objects which has a comparatively long life.

It is yet a further object of the present invention to provide an ion selective membrane which has low crystallinity.

It is yet another object of the present invention to provide a method of making an ion selective electrode construction which includes an ion selective membrane in accordance with the preceding objects.

It is still another object of the present invention to provide an ion selective electrode construction which includes an ion selective membrane in accordance with the preceding objects.

Accordingly, one embodiment of the present invention includes an ion selective membrane which comprises an ethylene vinylacetate (EVA) polymer. The EVA polymer includes from about 30 weight percent to about 75 weight percent vinylacetate monomer, from about 0% to about 20% plasticizer by weight and at least one ion selective material. The membrane is from about 0% crystalline to about 10% crystalline.

Another embodiment of the present invention includes an ion selective membrane comprised of ethylene monomers, vinylacetate monomers and monomers of at least one additional vinyl species having a charged site or a polar group. The polymer includes from about 35 weight percent to about 55 weight percent vinyl acetate monomer and is substantially devoid of plasticizer. The membrane additionally includes at least one ion selective material. The membrane is from about 0% crystalline to about 10% crystalline.

In a further embodiment of the present invention, an ion selective electrode construction is provided which includes at least one electrode and an ion selective membrane which is operatively positioned with respect to the electrode. The membrane comprises an ethylene vinylacetate polymer which includes from about 30 weight percent to about 75 weight percent vinylacetate monomer and from 0 per cent to about 20 per cent by weight plasticizer. The membrane further includes at least one ion selective material. The membrane is from about 0% crystalline to about 10% crystalline.

In yet another embodiment of the present invention, a method of forming an ion selective electrode construction for use in ion selective electrode determinations is provided. The method includes providing a reference electrode and positioning an ion selective membrane in operative position over the reference electrode. The membrane comprises an ethylene vinylacetate polymer which includes from about 30 weight percent to about 75 weight percent vinylacetate monomer and about 0% to about 20% plasticizer by weight. The membrane further comprises at least one ion selective material. The membrane is from about 0% crystalline to about 10% crystalline.

It is a feature of the present invention that ion selective membranes can be formed having comparatively long lifetimes. Moreover, in certain embodiments of the present invention, having a reduced amount of plasticizer in an ion selective membrane results in improved water uptake characteristics.

BRIEF DESCRIPTION OF THE DRAWINGS

The objects, advantages and features of the present invention will be more clearly appreciated from the following detailed description when taken in conjunction with the accompanying drawings, in which.

DETAILED DESCRIPTION

Figure 1:
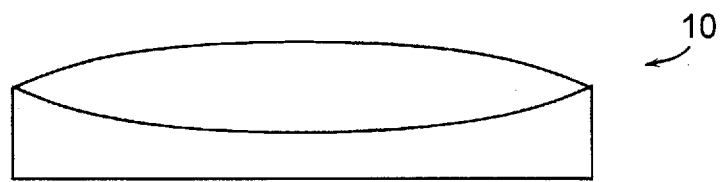
FIG. 1 is a cross-sectional view of an ion selective membrane in accordance with the present invention.
Figure 2:
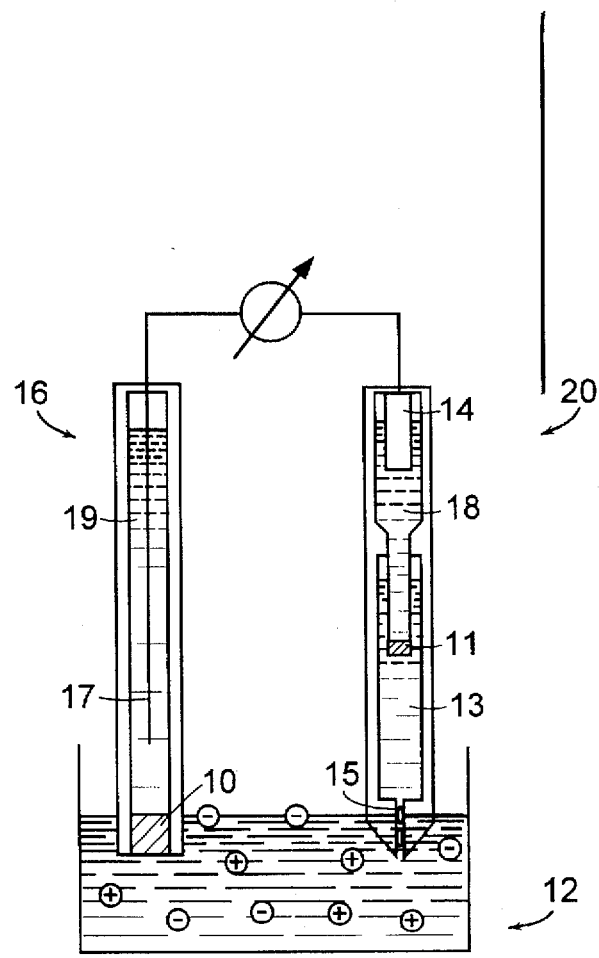
FIG. 2 is a cross-sectional view of an ion selective electrode construction in accordance with the present invention.

The present invention relates to ion selective membranes and ion selective electrode constructions as shown in FIGS. 1 and 2, respectively. FIG. 1 depicts an ion selective membrane 10 which, according to the present invention, has low crystallinity.

"Low crystallinity" is herein meant to refer to crystallinity from about 0% to about 10%, more preferably from about 0% to about 5% and most preferably from about 0% to about 3%. Crystallinity as used herein corresponds to polymer crystallinity as measured using x-ray powder diffraction such as disclosed in *Makrmol. Chemie* 50, 98(1961) and *J. Appl.Polym.Sci.* 14, 173 (1970). As known to those skilled in the art, there is a general correlation between the crystallinity of a polymeric material and the stiffness of the polymeric material. For ion selective membranes according to the present invention, the stiffness of membrane 10 has particularly advantageous values when membrane 10 has a crystallinity below about 10%.

Membrane 10 may have any stiffness so long as membrane 10 has low crystallinity. Membrane 10 should have a stiffness at least as great as that of a membrane comprised of 33% PVC and 66% plasticizer (NPOE or DOA). Preferably, membrane 10 has a G-modulus of from about 0.1 MegaPascal to about 2.0 MegaPascals, more preferably from about 0.3 MegaPascals to about 1.0 MegaPascals, and most preferably about 0.6 MegaPascals as measured using the DIN 53 455 method as disclosed in *Kunststoffe* 57, 321 (1967).

Typically, membrane 10 is sensitive to ions at concentration levels as disclosed in *Anal. Sci.* 4, 547(1988); *Anal. Chim. Acta* 255, 35 (1991); *J. Chem. Soc. Far. I* 82 1179 (1986); *Clinical Chemistry* 32, 1448 (1986); or *SPIE* 1510, 118(1991). For example, membrane 10 may be sensitive to concentration levels of at least about: $10^{-5.8}$ M for $NH_4^+$; $10^{-7.4}$ M for $Ca^{2+}$; $10^{-5.3}$ M for $Li^+$; $10^{-12}$ M for $H^+$; $10^{-5}$ M for $Mg^{2+}$ and $10^{-5.5}$ M for $Na^+$. Although particular ion selectivities have been disclosed herein, membrane 10 may have any ion selectivity so long as membrane 10 has low crystallinity.

Conventionally, the ion selectivity of membrane 10 is measured by two methods. In the separate solution method, a sensor is placed in many different solutions sequentially, and the potential in each solution is measured. Each solution contains only one type of ion and counter ion. The Nicolsky equation (given below) is then applied to the measured potentials of the known concentrations to calculate the selectivity coefficients. The slope is assumed to be constant. In the method of mixed solutions, both ions of interest and interfering ions are present. The concentration of one of these ions is varied while the other is held constant. The response is fit to the Nicolsky equation to give the selectivity coefficient. The Nicolsky equation is given by:

$$E=E_c+(RT/z_iF)ln([i]+k_{ij}[j]^{z_i/z_j}),$$

where $E_c$ is a constant, R is the gas constant, T is temperature in units of Kelvin, i is the ion of interest, j is the interfering ion, $z_i$ is the charge of the ion of interest, $z_j$ is the charge on the interfering ion, $k_{ij}$ is the selectivity coefficient, F is the Faraday constant, and $(RT/z_iF)$ is the slope of the membrane in units of millivolts (mV) per natural log of analyte concentration.

While the slope of membrane 10 may have any value so long as membrane 10 has low crystallinity, membrane 10 preferably has a slope of at least about $45/z_i$ mV per decade of analyte concentration, more preferably at least about $50/z_i$ mV per decade of analyte concentration and most preferably at least about $55/z_i$ mV per decade of analyte concentration.

FIG. 1 shows an embodiment of membrane 10 in which it is disk-like in shape. For such embodiments, membrane 10 preferably has a radius of from approximately 0.2 cm to approximately 0.4 cm. In certain embodiments of the present invention in which membrane 10 is used in a free standing electrode, membrane 10 preferably has a thickness from approximately 100 micrometers to approximately 300 micrometers. For certain embodiments of the present invention in which membrane 10 is a planar electrode, membrane 10 preferably has a thickness from about 10 micrometers to about 100 micrometers. Although certain dimensions of membrane 10 have been described herein, it is to be understood that membrane 10 may have any shape so long as it has low crystallinity.

The electrical resistivity of membrane 10 may be any so long as membrane 10 has low crystallinity. For membranes having a thickness of about 100 micrometers and an area of about 0.32 $cm^2$, the electrical resistivity is typically from about $10^4$ Ohms to about $5 \times 10^8$ Ohms, more preferably from about $10^4$ Ohms to about $2 \times 10^7$ Ohms.

Membrane 10 may have any lifetime so long as it has low crystallinity. Preferably, membrane 10 has a lifetime of at least 10 days with a slope of at least 85% of the theoretical value (based on the Nicolsky equation), more preferably at least 15 days with a slope of at least 85% of the theoretical value, and most preferably at least 20 days with a slope of at least 85% of the theoretical value as measured by an accelerated aging test. The accelerated aging test includes storing the material of which the membrane is comprised under pressure in water at 115° C., preparing a membrane from the material at least every two days, and testing the slope of the membrane at room temperature.

According to the present invention, membrane 10 comprises an EVA copolymer and at least one ion selective material. In certain embodiments, membrane 10 may also include a plasticizer, PVC, a salt or a combination thereof. It is to be appreciated that membrane 10 may include various combinations of these or other materials appropriate for use in ion selective membranes so long as membrane 10 has low crystallinity.

By "copolymer" it is herein meant to refer to a polymerization product containing more than one monomer unit. For example, the monomer units of copolymers may be arranged such that the copolymers are selected from an illustrative and nonlimiting list which includes alternating copolymers, random copolymers, block copolymers and graft copolymers. In addition, copolymers according to the present invention may be arranged such that the copolymers include, but are not limited to, linear copolymers, branched copolymers (including star copolymers, comb copolymers, ladder copolymers and semiladder copolymers) and network copolymers. While certain types of copolymers have been disclosed herein, these lists are not limiting and any copolymer may be used according to the present invention so long as membrane 10 has low crystallinity.

According to the present invention, membrane 10 may include a normal EVA copolymer, a modified EVA copolymer, a functionalized EVA copolymer or a modified, functionalized EVA copolymer. Preferably, membrane 10 includes a normal EVA copolymer, a modified EVA copolymer or a functionalized EVA copolymer. More preferably, membrane 10 includes a normal EVA copolymer. By "normal EVA copolymer" it is herein meant to refer to an EVA copolymer which has substantially all carbon atoms in its backbone and is comprised of substantially all ethylene and vinyl acetate monomer units. "Modified EVA copolymers" herein denote EVA copolymers which include noncarbon atoms in their backbone structures such as, for example, O, S, N or atoms. A "functionalized EVA copolymer" herein refers to an EVA copolymer which includes functional groups other than those of ethylene and vinyl acetate. A "modified, functionalized EVA copolymer" herein refers to an EVA copolymer which is both a modified EVA copolymer and a functionalized EVA copolymer as defined herein. Although certain types of EVA copolymers have been disclosed herein it is to be appreciated that any EVA copolymer may be used according to the present invention so long as membrane 10 has low crystallinity.

The dielectric constant of EVA usually increases as the weight percent of vinyl acetate in the EVA increases as disclosed in *Vysokomol. Soyed.* A15, 1382 (1972) and *Kunstsoffe* 57, 321 (1967). Preferably, the dielectric constant of membrane 10, which comprises normal EVA, is from about 2.8 to about 4.5, more preferably from about 3 to about 4.5 and most preferably from about 3.3 to about 4.5. For embodiments of the present invention which include modified EVA and/or functionalized EVA, the dielectric constant of membrane 10 may be as high as about 30 or as low as about 2.8. However, it is to be appreciated that the dielectric constant of membrane 10 may have any value so long as membrane 10 has low crystallinity.

The molecular weight of EVA copolymers appropriate for use according to the present invention is preferably from about 40,000 Daltons to about 500,000 Daltons, more preferably from about 100,000 Daltons to about 400,000 Daltons and most preferably about 250,000 Daltons as measured using the methods disclosed in *Br. J. Polym.* 1, 225 (1969). However, it is to be appreciated that EVA copolymers having other molecular weights may also be used so long as membrane 10 has low crystallinity.

EVA copolymers appropriate for use in the present invention may have any second order transition temperature so long as membrane 10 has low crystallinity. Preferably, EVA copolymers have a second order transition temperature of from about −15° C. to about −45° C., more preferably from about −15° C. to about −35° C. and most preferably from about −20° C. to about −30° C. as measured according to DIN 53 513 or as disclosed in *Kautschuk u. Gummi Kunststoffe* 22, 116 (1969).

For embodiments of membrane 10 which include a plasticizer, EVA copolymers preferably include from about 30 weight percent to about 75 weight percent vinyl acetate monomers, more preferably from about 40 weight percent to about 50 weight percent vinyl acetate monomers, and most preferably about 45 weight percent vinyl acetate monomers. However, these ranges should not be construed as limiting. The weight percent of vinyl acetate for EVA used in membrane 10 for such embodiments may be any so long as membrane 10 has low crystallinity.

According to embodiments of the present invention in which membrane 10 includes about 0% plasticizer by weight (i.e., membrane 10 is "substantially devoid of plasticizer"), EVA copolymers preferably include a weight percentage of vinyl acetate from about 30 percent to about 55 percent, more preferably from about 40 percent to about 50 percent vinyl acetate monomer, and most preferably from about 45 percent vinyl acetate monomer. However, it is to be appreciated that EVA copolymers appropriate for use in these embodiments may comprise any mole percentage of vinyl acetate so long as membrane 10 has low crystallinity.

It should be noted that having a reduced amount of plasticizer in membrane 10 usually increases the adhesive properties thereof relative to most known membranes used in ion selective electrodes. For certain embodiments, the increased adhesion of membrane 10 may be advantageous such as, for example, when membrane 10 is used in a planar ion selective device. Other embodiments for which relatively high adhesion for membrane 10 is advantageous are known to those skilled in the art and are intended to be within the scope of the present invention.

EVA copolymers according to the present invention may be synthesized using techniques such as disclosed in *Br. Polym. J.* 1, 225 (1969), *Kautschuk u. Gummi Kunstsoffe* 22, 116(1969), U.S. Pat. No. 3,325,460 and German Patent No. 1,126,613. These methods include, for example, high pressure radical reaction of vinyl acetate and ethylene (at pressures from about 1500 to about 2000 atmospheres), moderate pressure radical polymerization of vinyl acetate and ethylene (at pressures from about 100 to about 500 atmospheres) or emulsion polymerization. High pressure radical polymerization typically produces EVA having up to about 40% vinyl acetate by weight. Medium pressure polymerization usually results in EVA which has from about 30% to about 100% vinyl acetate by weight. Emulsion polymerization can produce EVA having an amount of vinyl acetate which covers the whole range, but the product can be highly branched or even cross-linked. Preferably, medium pressure polymerization is used to synthesize EVA. Other methods of synthesizing EVA are known to those skilled in the art and are intended to be within the scope of the present invention. Such techniques are limited only in that, when the resulting EVA is incorporated into membrane 10, membrane 10 has low crystallinity.

Methods of synthesizing modified and/or functionalized EVA copolymers appropriate for use in the present invention are known to those skilled in the art and are intended to be within the scope of the present invention. For example, incorporation of non-vinyl acetate, vinyl monomers and non-ethylene monomers can be accomplished by forming copolymers according to standard methods. Carbon monoxide (CO) can be polymerized with ethylene and vinyl acetate such as disclosed in *Vysokomol. Soyed.* A11, 2585 (1969). Using these methods, copolymers including ethylene, vinyl acetate and carbon monoxide with up to 70 mole percent carbon monoxide can be produced without substantially changing the crystallinity or elasticity of the material.

*J.Polym.Sci.* A11, 9, 3083 (1971) discloses methods of polymerizing a variety of compounds with ethylene and vinyl acetate such as, for example, vinyl chloride, vinyl fluoride, propylene and hexene-1. Any of these methods and copolymers may be used according to the present invention so long as membrane 10 has low crystallinity. However, it should be noted that the crystallinity of the copolymer depends upon the monomer polymerized with ethylene and vinyl acetate. Therefore, when vinyl chloride and vinyl fluoride are incorporated into the copolymer, up to about 50 mole percent of the additional monomer may be included in the copolymer. About 31 mole percent of propylene may be used, and the amount of hexene-1 used may be based on the fact that hexene-1 has substantially the same crystallinity as vinyl acetate. It should be further noted that, in certain embodiments, incorporating these monomers into the copolymer may change the dielectric constant of the overall polymer.

*Vysokomol. Soyed.*A11, 2585 (1969) discloses compounds that can be copolymerized with ethylene to form copolymers. These compounds include vinylene carbonate, maleic anhydride and organic esters of phosphinic acid. Typically, the monomers which are polymerized with ethylene and vinyl acetate are capable of resulting in a copolymer with a lower crystallinity than EVA. However, it should be noted that not all these additives cause a substantial change to the crystallinity of the copolymer. Accordingly, for those monomers which do not assist in decreasing the crystallinity of the overall material, they are typically present in amounts of less than about 5% of the overall material by weight. However, it is to be appreciated that the amount of the monomer polymerized with ethylene and vinyl acetate is limited only in that, when membrane 10 comprises the resulting copolymer, membrane 10 has low crystallinity.

Other copolymers are known to those skilled in the art and include monomer units of, for example, 4-ethylidene-2-nobornene, 5-ethylidene-2-nobornene, hexaydrodimethanonaphthalene, N-methylacryalamide cyanurate, methylmethacrylate, methylene succinic acid, and ethylene oxide with S-trioxone. Many of the monomers which may be used to use copolymers with ethylene and vinyl acetate are capable of introducing heteroatoms (i.e., non-carbon atoms) into the backbone of the copolymer.

Ionomers appropriate for use in the present invention can also be made from EVA synthetic methods using copolymerization in which charge groups are introduced as pendant side chains as described in *Kunststoffe* 57, 321 (1967). For such embodiments, the copolymer preferably includes from about 0.001% to about 5% of the ionized charge group by weight, more preferably from about 0.1% to about 4% and most preferably 0.5% to about 2%. However, it is to be understood that the amount of the ionized charged group within copolymers which may be included in membrane 10 are limited only in that membrane 10 should have low crystallinity.

According to the present invention, membrane 10 may include EVA which has PVC grafted thereto. Methods of synthesizing such copolymers are known to those skilled in the art and include those disclosed in, for example, *Br. Polym. J.* 1, 225, (1969). Typically, such copolymers include up to 50% grafted PVC by weight, more preferably less than about 10%.

EVA copolymers appropriate for use in the present invention may also be synthesized by hydrolyzing the acetate group in vinyl acetate to yield vinyl alcohol. It should be noted that, as disclosed in *J. Polym. Sci.* A1, 3083(1971), essentially all forms of ethylene vinyl alcohol have some crystallinity. Accordingly, according to the present invention, copolymers containing vinyl alcohol monomers preferably include less than about 20% vinyl alcohol by weight.

Ion selective materials appropriate for use according to the present invention should make membrane 10 permselective. Such materials are capable of complexing a desired ion and extracting an ion of one charge without extracting an ion of opposite charge. These ion selective materials include, for example, nondissociable, ion-specific ligands, i.e., ionophores, or electrically charged liquid ion-exchangers. Ion selective materials are known to those skilled in the art and, in the present invention, are limited in their type and mole percent of membrane 10 only by the fact that membrane 10 and should have low crystallinity.

Preferably, membrane 10 comprises from about 0.05 percent to about 10 percent of ion selective material by weight, more preferably from about 1 percent to about 6 percent ion selective material by weight, most preferably from about 1 percent to about 3 percent ion selective material by weight. In certain embodiments, more than one ion selective material may be incorporated into membrane 10. In embodiments of the present invention which include more than one ion selective material, membrane 10 preferably comprises from about 0.05 percent to about 10 percent ion selective material by weight, more preferably from about 1 percent to about 6 percent by weight and most preferably from about 1 percent to about 3 percent by weight. However, it is to be understood that membrane 10 may comprise any amount of ion selective material and any number of ion selective materials so long as membrane 10 has low crystallinity.

Ion selective materials according to the present invention may be any of those known to be selective towards a particular ion to be analyzed. An illustrative and nonlimiting list of such ion selective materials includes: for potassium, valinomycin, bis(benzo-15-crown-5)-4-ylmethyl)pimelate dicyclohexano-18-crown-6, dibenzo-18-crown-6, tetraphenyl borate, tetrakis (p-chlorophenyl) borate, cyclopolyethers, tetralactones macrolide actins (monactin, nonactin, dinactin, trinactin), the enniatin group (enniatin A, B), cyclohexadepsipeptides, gramicidine, nigericin, dianemycin, nystatin, monensin, esters of monensin, antamanide, alamethicin (cyclic polypetieds); for calcium, ETH1001 (as disclosed in *Anal. Chem.* 53, 1970(1981), ETH129, A23187 (Fluka of Buchs, Switzerland), ETH 5234 (Fluka of Buchs, Switzerland), bis (didecylphosphate), bis (4-octylphenylphosphate), bis(4-(1,1,3,3-tetramethylbutyl)) phenylphosphate, tetracosamethylcyclododecasiloxane, N,N'-di((11-ethoxycarbonyl) undecyl)-N,N'4, 5-tetramethyl-3,6-dioxaoctane diamide, antibiotic A-23187 (as disclosed in *Ann. Rev. Biochem.* 45, 501(1976)); for hydrogen, ETH1907 (Fluka of Buchs, Switzerland), ETH1778 (Fluka of Buchs, Switzerland), tridodecylamine, ETH1907, N-methyl n-octadecyl(1-methyl,2-hydroxy,2-phenyl)ethylamine, N-octadecyl 3-hydroxy N propylamine, N,N'bis(octadecyl ethylene amine),p-octadecyloxy-m-chlorophenylhydrazonemeso oxalonitrile; for sodium, monensin, ETH227 (Fluka of Buchs, Switzerland), ETH157 (Fluka of Buchs, Switzerland), ETH2120 (Fluka of Buchs, Switzerland), ETH4120 (Fluka of Buchs, Switzerland), ETH227, ETH157, $NAS_{11-18}$,N,N',N"-triheptyl-N,N',N"-trimethyl-4,4',4"-propylidintris-(3-oxabutyramide), 4-octadecanoyloxymethyl-N,N,N',N'-tetracyclohexyl-1,2-phenylenedioxydiacetamide, bis[(12-crown-4)methyl] dodecylmethylmalonate, ETH149, ETH1810, cyclopolyethers; for lithium,N,N'-diheptyl-N,N',5,5-(tetramethyl-3,7-dioxononanediamide), ETH149 (Fluka of Buchs, Switzerland), ETH1644 (Fluka of Buchs, Switzerland), ETH 1810 (Fluka of Buchs, Switzerland), ETH2137 (Fluka of Buchs, Switzerland), 6,6-dibenzyl-14-crown-4; 6,6-dibenzyl-1,4,8,11-tetraoxa-cyclotetradecane (Fluka of Buchs, Switzerland), 6[2-(diethlphosphonoox)ethyl]6-dodecyl-14-crown-4 (Fluka of Buchs, Switzerland), 12-crown-4,6,6-dibenzyl-14 chrown-4, cyclopolyethers, dodecylmethyl 14-crown-4; for chloride, tridodecyl ammonium salt, 5,10,15,20-tetraphenyl-21H, 23H-porphin manganese (111) chloride (Fluka of Buchs, Switzerland), quaternary ammonium chloride and tributyl tin chloride; for rubidium, cyclopolyethers; for cesium, cyclopolyethers; for $HCO_3^-$, trifluoroacetyl-p-alkylbenzenes; for $NH_4^+$, nonactin, monactin; for $NO_3^-$, tridodecylammonium chloride; and for $Mg^{2+}$, ETH 7025 (Fluka of Buchs, Switzerland or as disclosed in *Anal. Chem.* 341, 727(1991)), ETH1117 (Fluka Buchs of Switzerland), ETH5214 (Fluka Buchs of Switzerland), ETH4030 (Fluka of Buchs, Switzerland) and ETH5214. Preferably, the ion selective materials include: for potassium, valinamycin; for calcium, ETH1001; for $NH_4^+$, nonactin; for hydrogen, triododecylamine; for $NO_3^-$, tridodecylammonium chloride; for $Cl^-$, tridodecyl ammonium salt; and for sodium, ETH2120 (Fluka of Buchs, Switzerland). All ETH compounds are as disclosed in *Anal. Sci.* 4, 547 (1988) unless otherwise noted.

A "plasticizer" as used herein refers to a material which can be added to membrane 10 to reduce the stiffness thereof. Typically, such plasticizers comprise polymeric materials, organic solvents or oils which are generally known in the art as external plasticizers (i.e., not chemically incorporated into the backbone of the EVA copolymer). An illustrative and nonlimiting list of plasticizers appropriate for use in the present invention includes dioctyl adipate (DOA) nitrophenyl octylether (NPOE), dimethyl phthalate, dioctylphenylphosphonate, dibutyl phthalate, hexamethyl phosphoramide, dibutyl adipate, diundecyl phthalate, and dioctyl sebacate (DOS). Other plasticizers are known to those skilled in the art and may be used according to the present invention so long as membrane 10 has low crystallinity.

For certain embodiments, a plasticizer can be selected based on the ion for which membrane 10 is selective. In such cases, the plasticizer may be selected by performing a test of ion selectivity and slope of response to the ion of interest. For example, when membrane 10 is intended to be selective for potassium, DOA and DOS are preferably used as plasticizers, and when membrane 10 is designed to be selective towards calcium, NPOE is the preferred plasticizer. Other plasticizers appropriate for use in membrane 10 when designed to be selective for certain ions are known to those skilled in the art and are meant to be within the scope of the present invention. Moreover, a plasticizer need not be selected based on the ion toward which membrane 10 is selective. It is to be appreciated that the use of plasticizers in ion selective membranes according to the present invention can result in ion selective membranes which have relatively long lifetimes as measured according to methods disclosed herein.

In some embodiments, it may be desirable to improve the ion transference characteristics and permselectivity of membrane 10 by adding a salt thereto. In embodiments of the present invention which include salts, the salt preferably has a mole percent of membrane 10 from about 10% to 80% of the mole percent of the ion selective material, more preferably from about 33% to 66% of the mole percent of the ion selective material and most preferably about 50% of the mole percent of the ion selective material. In certain embodiments, the added salt may also serve as an integral part of the ion selective material. For such embodiments, the amount of salt within membrane 10 should not exceed the amount of ion selective material included within membrane 10 as disclosed elsewhere herein. Preferably, the salt is $KB(C_6H_4X)_4$ where X is H, F or $CF_3$. For all embodiments, the amount of salt included within membrane 10 is limited only in that membrane 10 should have low crystallinity.

Addition of salts to membrane 10 may be carried out by several methods. In certain embodiments, such salts may act as ion selective materials. According to one method, membrane 10 is cast as a free-standing material which is soaked in an aqueous solution comprising the salt to be added. Typically, such an aqueous solution has a salt concentration from about 1 mM to about 1M. Preferably, the polymer and the salt to be added are dissolved in a solvent. The salt can be at the desired mole percent relative to the polymer. The dissolved polymer and salt may then be cast. The materials of membrane 10 may be drop cast or spin cast from a solution including the salt. While some methods of incorporating salts into membrane 10 have been disclosed herein, other methods are known to those skilled in the art and are within the scope of the present invention.

Ion selective membranes in accordance with the present invention may be made according to any method so long as membrane 10 has low crystallinity. In one embodiment of the present invention, membrane 10 is prepared by dissolving an EVA copolymer in a first solvent. A solution containing the ion selective material(s) and a second solvent is then added to the EVA copolymer containing solution. The order of mixing of the above-mentioned solutions may be reversed in some embodiments. In addition, the EVA copolymer and ion selective material(s) may be dissolved within the same solvent. The resulting solution including the EVA copolymer and the ion selective material(s) is molded according to standard methods to form membrane 10 such as, for example, standard solvent casting methods. It is to be appreciated that while certain methods of forming a membrane according to the present invention have been disclosed herein, other methods of forming membrane 10 will be apparent to those skilled in the art and are intended to be within the scope of the present invention.

Solvents appropriate for use in the present invention are limited only to the extent that they should be capable of dissolving the EVA copolymer and other components of membrane 10 without changing the chemical structure of the EVA copolymer or other materials of which membrane 10 is comprised. Typical solvents include tetrahydrofuran (THF), carbon tetrachloride, chloroform, methylene chloride, p-xylene and toluene. Preferably, the solvent is THF. Other solvents having the aforementioned properties, such as halogenated hydrocarbons and aromatic solvents, may also be used and are known to those skilled in the art.

For embodiments of the present invention which incorporate PVC, a plasticizer or other materials appropriate for use in membrane 10, these materials may first be dissolved in a solvent as described above and subsequently mixed with the EVA/ion selective material(s) solution. Alternatively, the order of mixing may be reversed. In addition, all the materials including the EVA copolymer and ion selective material(s) may be dissolved within the same solvent. The resulting solution may be molded as given above to form membrane 10, or other methods of forming such membranes which are known to those skilled in the art may be used.

FIG. 2 depicts an ion selective electrode cell construction 20 in accordance with the present invention. Ion selective electrode construction 20 includes ion selective membrane 10, analyte solution 12, reference electrode 14, and ion-selective electrode 16. Reference electrode 14 includes saturated solution 18, junction 11, bridge electrolyte 13 and capillary 15. Ion selective electrode 16 includes membrane 10, contact electrode 17 and internal solution 19.

Reference electrode 14 preferably provides precision to the voltage stability to less than 100 microvolts which can allow the precision of the concentration measurement to be about 1%. Such reference electrodes include the Ag/AgCl electrode, the calomel electrode, Ag/Ag oxide electrodes and other oxide electrodes. It should be noted that, when using an oxide electrode with a limited volume electrode reservoir, a pH buffer solution having a value near that of the analyte solution 12 should be used. Such buffer solutions are known to those skilled in the art and are intended to be within the scope of the present invention. Moreover, while one particular configuration of construction 20 is depicted in FIG. 2, other constructions appropriate for use in the present invention will be apparent to those skilled in the art and are intended to be within the scope of the present invention. These components may be any arrangement so long as ion selective electrode construction 20 operates to measure to the concentration of the analyte in analyte solution 12.

Inner reference electrode 17 may be, for example, an Ag, Pt, C, Iridium oxide or Ag/AgCl electrode, or the insulator of a field effect type electrode such as silicon nitride, silicon dioxide or alumina. In addition, inner reference electrode 17 may contact a solid electrolyte, a polymer electrolyte or a polymer membrane disposed between inner reference electrode 17 and membrane 10. Moreover, inner reference membrane 17 may be a polymer with a redox couple attached thereto. Furthermore, inner reference electrode 17 may be a polymer with a redox couple blended (mixed) therein. Inner reference electrode 17 may also be a planar fabricated electrode such as disclosed in U.S. Pat. No. 4,734,184. Other embodiments of inner electrode 17 will be apparent to those skilled in the art and are intended to be within the scope of the present invention.

Analyte solution 12 includes the ion to be detected (i.e., the analyte) and a solvent. Solvents which can be used are limited only in that they should dissolve the analyte, not dissolve membrane 10 and not interfere with the measurement of the analyte concentration or chemically react with membrane 10 or any other portion of construction 20. Typically, the solvent includes water. Such solvents include, but are not limited to, water, blood, urine, and other aqueous solutions.

In certain embodiments, it is advantageous to buffer analyte solution 14 to have a constant ionic strength. When analyte solution 12 is buffered in calibration solutions, it is done to match the ionic strength of the sample. For example, if analyte solution 12 comprises blood, the solution would typically be buffered to 0.15M. In river water, the ionic strength may be buffered to be from about $10^{-4}$ to about $10^{-3}$M. For $Ca^{2+}$ electrodes, analyte solution 12 is often buffered to 0.33M. Buffering a solution is usually accomplished by adding a salt to analyte solution 12 to buffer the ionic strength. The ionic strength of an ion in solution is given by $$\mu = \frac{1}{2}\Sigma[C_i^{Z_i}]Z_i^2$$

where $\mu$ is the ionic strength of the ion used to buffer the solution, $c_i$ is the concentration of the ion used to buffer the solution and $z_i$ is the charge on the ion used to buffer the solution. Such salts are limited only in that they should not interfere with the measurement of the concentration of the analyte. The particular salt used depends upon the analyte. For example, for measurements of $Ca^{2+}$ and $K^+$ in blood, the salt is often NaCl. To measure sodium, potassium chloride may be used. For $Cl^-$ measurements, $HCO_3^-$ is typically used, and for $H^+$ many different buffer salts may be used. The particular buffer salt used is limited only in that it should allow an accurate measurement of the concentration of analyte in analyte solution 12.

Certain embodiments of the present invention include internal solution 19. Typically, internal solution 19 includes a salt and a solvent. Salts which may be used in internal solution 19 include, but are not limited to, NaCl, KCl and $CaCl_2$ which may be used with Ag/AgCl electrodes or calomel electrodes. Internal solution 19 should include a concentration of from about 0.1 mM to about 0.5M of the analyte. Preferably, this ion is in the form of the chloride salt.

The solvent used for internal solution 19 should not interfere with the measurement of the analyte or alter the chemical structure of membrane 10 or any other portion of construction 20. Such solvents are typically polar solvents including aqueous solutions. Preferably, the solvent is water.

It is to be appreciated that ion selective membranes in accordance with the present invention can be incorporated into field effect transistors. Such transistors typically would include a layer of semiconductor material, a pair of diffusion regions, another diffusion region having a doping characteristic different from the pair of diffusion regions, an electrically insulating material provided on the semiconductor material, an ion selective membrane separated from the diffusion regions by the insulating material, and an electrically insulating encapsulant sealing the transistor. The encapsulant seals the transistor from a sample region while leaving the ion selective membrane exposed to a particular sample. Other such chemical-responsive transducers capable of having an ion selective membrane in accordance with the present invention incorporated therein will be apparent to those of skill in the art and are intended to be within the scope of the present invention.

EXAMPLE 1

A membrane according the present invention including 96.7% EVA(45), 3% valinomycin and 0.3% $KB(C_6H_4Cl)_4$ by weight was prepared as follows. 6.5 ml of EVA (45) (Item number 784 obtained from Scientific Polymer Products, Ontario, N.Y. 14519, molecular weight of 260,000 as measured by gel permeation chromatography, melt index of 2–5 measured according to ASTM D 1238-62 T, softening point of 182° C.) dissolved in distilled tetrahydrofuran (THF) (obtained from Aldrich Chemical Co. located in Milwaukee, Wis.) to a concentration of 30 mg\ml was mixed with 3 ml of valinomycin (purchased from Sigma located in St. Louis, Mo.) dissolved in THF to a concentration of 2 mg\ml. 0.6 ml of $KB(C_6H_4Cl)_4$ (purchased from Fluka of Buchs, Switzerland) dissolved in THF to a concentration of 1 mg\ml was added to the EVA (45)/valinomycin solution. This EVA/45 valinomycin/$KB(C_6H_4Cl)_4$ solution was mixed with a magnetic stir bar for one hour at room temperature under atmospheric pressure. The solution was then filtered to remove impurities. About 3–5% of the mass was lost during the filtration, and the filtered solutions had concentrations of about 35 mg/ml. The solution was then cast in a Teflon mold having a 3.82 centimeter diameter according to the method disclosed in *J. Chem Educ.* 51, 541 (1974). The membrane was dried for 48 hours and smaller diameter circles were then cut out of the membrane and then mounted in Phillips-type electrode body for testing as ion selective electrodes using the construction depicted in FIG.2.

An internal 0.01M KCl solution with a Ag/AgCl reference electrode was used, and an external saturated calomel electrode served as the other reference electrode.

The membranes were tested in aqueous solution with varying $K^+$ concentration and ionic strength buffered to 0.1M with NaCl. Interferences were calculated using the Nicolsky equation at $10^{-4}$ and $10^{-5}$M KCl in 0.1M NaCl. This membrane gave a slope of 58 mV per decade of $K^+$ concentration and ion selectivity of log $k_{ij}=-4.0$ as measured using the method described herein.

EXAMPLE 2

$Ca^{2+}$ membranes were made according to the method and using the materials as disclosed in Example 1, substituting an equal amount of ETH1001 (Molecular formula $C_{38}H_{72}N_2O_8$, molecular weight 685.01, selectophore grade, purchased from Fluka of Buchs, Switzerland) for valinomycin. The resulting membrane gave a slope of 28 mV per decade of $Ca^{2+}$ concentration, and an ion selectivity of log $k_{ij}=-4.0$ against $Na^+$. These measurements were made using the technique disclosed in Example 1, with the exceptions that the internal solution was $CaCl_2$, 0.33M NaCl was used to adjust the ionic strength to 0.1M, and the concentration of $CaCl_2$ was varied.

EXAMPLE 3

$NH_4^+$ ion-selective membranes were made using the method and the materials disclosed in Example 1 by substituting nonactin (purchased from Sigma located in St. Louis, Mo.) for valinomycin. The slope of the membrane was 58 mV per decade of $NH_4^+$ concentration and the interference by $Na^+$ had a value of log $k_{ij}=-2$. These measurements were made using the method of Example 1 with the exception that the internal solution was $NH_4Cl$, NaCl was used to adjust the ionic strength to 0.1M, and the concentration of $NH_4Cl$ was varied.

EXAMPLE 4

A membrane comprising 29% PVC (obtained from Fluka of Buchs, Switzerland) 49.1% EVA (45), 20% dioctyl adipate (DOA) (selectophore grade from Fluka of Buchs, Switzerland), 1% valinomycin and 0.1% KB $(C_6H_4Cl)_4$ (obtained from Fluka of Buchs, Switzerland) by weight was prepared as follows. 3.25 ml of EVA (45) having a concentration of 30 mg/ml was mixed with 1 ml of a valinomycin solution having a concentration of 2 mg/ml. 0.2 ml of $KB(C_6H_4Cl)_4$ having a concentration of 1 mg/ml was added to the solution. 39 mg of DOA and 56.5 mg of PVC, previously dissolved in 3 ml of distilled THF, was added to this solution. The solution was cast in a Teflon mold and the membranes were tested as described in the above examples. A membrane electrode slopes of 57 mV per decade of $K^+$ concentration and an ion selectivity of log $k_{ij}=-3.8$ against $Na^+$ were obtained. All materials and methods were the same as in Example 1 unless otherwise noted. Unless otherwise mentioned, the vendors for particular chemical species listed in the examples are the same as those noted in earlier examples.

EXAMPLE 5

In example 5, as in examples 1–4 which used EVA(45), it is believed that the crystallinity of the membranes are below about 3%.

| % PVC | % DOA | % EVA | % val | % KB(ClPh)$_4$ | slope(mV) | log $k_{ij}$ |
|---|---|---|---|---|---|---|
| 29 | 20 | 50 | 1 | 0.1 | 57 | −3.8 |
| 29 | 0 | 70 | 1 | 0.3 | 49 | −3.5 |
| 29 | 0 | 68 | 3 | 0.3 | 53 | −4.0 |
| 0 | 0 | 99 | 1 | 0 | 51 | −2.2 |
|  |  | 99 | 1 | 0.1 | 55 | −3.5 |
|  |  | 99 | 1 | 0.2 | 55 | −3.4 |
|  |  | 99 | 1 | 0.3 | 58 | −4.0 |
|  |  | 98 | 2 | 0 | 42 | −3.1 |
|  |  | 98 | 2 | 0.1 | 57 | −3.3 |
|  |  | 98 | 2 | 0.2 | 57 | −3.6 |
|  |  | 98 | 2 | 0.3 | 56 | −3.4 |
|  |  | 97 | 3 | 0.1 | 55 | −3.0 |
|  |  | 97 | 3 | 0.2 | 54 | −2.1 |
|  |  | 94 | 6 | 0.3 | 55 | −3.1 |
|  |  | 93 | 6 | 0.6 | 58 | −2.5 |

EXAMPLE 6

In example 6, which uses EVA(45), it is believed that the crystallinity of the membranes are below about 3%.

| % PVC | % NPOE | % EVA | % ETH(1001) | % KB(ClPh)$_4$ | slope(mV) | log $k_{ij}(Na+)$ |
|---|---|---|---|---|---|---|
| 29 | 20 | 50 | 1 | 0.1 | 27 | −3.7 |
| 29 | 10 | 60 | 1 | 0.2 | 25 | −3.7 |
| 29 | 0 | 70 | 1 | 0.1 | 18 | −3.3 |
| 29 | 0 | 68 | 3 | 0.3 | 23 | −3.4 |
| 9 | 0 | 88 | 3 | 0.3 | 28 | −3.7 |
| 0 | 0 | 97 | 3 | 0.3 | 28 | −4.0 |
|  |  | 94 | 6 | 0.3 | 29 | −3.7 |
|  |  | 93 | 6 | 0.6 | 29 | −4.1 |
|  |  | 99 | 1 | 0.1 | 28 | −3.8 |
|  |  | 99 | 1 | 0.2 | 28 | −3.8 |

Having thus described certain embodiments of the invention, various alterations, modifications and improvements will readily occur to those skilled in the art. Such alterations, modifications, and improvements are intended to be part of this disclosure and are intended to be within the spirit and scope of the invention. The materials employed, as well as their shapes and dimensions, may be any required. Accordingly, the foregoing description is by way of example only and is not intended as limiting. The invention is limited only as defined in the following claims and the equivalents thereto.

What is claimed is:

1. An ion selective membrane, comprising:
   an ethylene vinyl acetate polymer, said polymer including from about 30 weight percent to about 75 weight percent vinyl acetate monomer and from about 0 percent to about 20 percent by weight plasticizer; and
   an ion selective material dispersed within the ethylene vinyl acetate polymer, wherein said ion selective membrane is from about 0% crystalline to about 10% crystalline.

2. An ion selective membrane in accordance with claim 1, wherein said polymer includes from about 35 weight percent to about 55 weight percent vinyl acetate monomer and from about 0 percent to about 5 percent by weight plasticizer.

3. An ion selective membrane in accordance with claim 2, wherein said polymer is substantially devoid of plasticizer.

4. An ion selective membrane in accordance with claims 1, 2 or 3, wherein said polymer includes from about 40 weight percent to about 50 weight percent vinyl acetate monomer.

5. An ion selective membrane in accordance with claims 1, 2 or 3, wherein said polymer includes about 45 weight percent vinyl acetate monomer.

6. An ion selective membrane in accordance with claims 1, 2 or 3, further comprising a salt uniformly incorporated in said membrane, said salt having a mole percent of said membrane so as to permit increased ion transport within said membrane.

7. An ion selective membrane in accordance with claim 6, wherein said mole percent of said salt is from about 10 percent to about 80 percent of said mole percent of said ion selective material.

8. An ion selective membrane in accordance with claim 6, wherein said mole percent of said salt is from about 33 percent to about 66 percent of said mole percent of said ion selective material.

9. An ion selective membrane in accordance with claims 1, 2 or 3, wherein said membrane has a slope of at least about 50 millivolts per decade of analyte concentration.

10. An ion selective membrane in accordance with claims 1, 2 or 3, wherein said membrane has a slope of at least about 55 millivolts per decade of analyte concentration.

11. An ion selective membrane in accordance with claims 1, 2 or 3, wherein said membrane is from about 0% crystalline to about 5% crystalline.

12. An ion selective membrane in accordance with claims 1, 2 or 3, wherein said membrane is from about 0% crystalline to about 3% crystalline.

13. An ion selective membrane in accordance with claim 2, wherein said membrane comprises from about 0.1 percent to about 10 percent of said ion selective material by weight.

14. An ion selective membrane in accordance with claim 13, wherein said membrane comprises from about 1 percent to about 6 percent of said ion selective material by weight.

15. An ion selective membrane in accordance with claim 1, further comprising:

polyvinyl chloride polymer combined with said ethylene vinyl acetate polymer, wherein said membrane comprises from about 0.1 percent to about 50 percent by weight said polyvinyl chloride polymer.

16. An ion selective membrane, comprising:

a polymer formed from the polymerization product of:

ethylene monomers;

vinyl acetate monomers; and monomers of at least one additional vinyl species having a charged site or a polar group, said polymer including from about 30 weight percent to about 55 weight percent vinyl acetate monomer, said polymer being substantially devoid of plasticizer; and an ion selective material dispersed within the polymer, wherein said ion selective membrane is from about 0% crystalline to about 10% crystalline.

17. An ion selective membrane in accordance with claim 16, wherein said charged site or said polar group is selected from the group consisting of carboxyl groups, amino groups, cyano groups, and hydroxyl groups.

18. An ion selective membrane in accordance with claim 16, wherein said polymer comprises at most about 5 percent by weight said monomers of said at least one additional vinyl species.

19. An ion selective membrane in accordance with claim 16, wherein said membrane is from about 0% crystalline to about 5% crystalline.

20. An ion selective membrane in accordance with claim 16, further comprising:

polyvinyl chloride polymer combined with said ethylene vinyl acetate polymer, wherein said membrane comprises from about 0.1 percent to about 50 percent by weight said polyvinyl chloride polymer.

21. An ion selective membrane in accordance with claim 16, wherein said membrane comprises from about 0.1 percent to about 10 percent of said ion selective material by weight.

22. In an ion selective electrode construction comprising at least one electrode, and an ion selective membrane operatively positioned with respect to said electrode, said membrane comprising:

an ethylene vinyl acetate polymer, said polymer having from about 30 weight percent to about 75 weight percent vinyl acetate monomer and from about 0 percent to about 20 percent by weight plasticizer; and an ion selective material dispersed within the ethylene vinyl polymer, wherein said ion selective membrane is from about 0% crystalline to about 10% crystalline.

23. An ion selective electrode construction in accordance with claim 22, wherein said polymer includes from about 0 weight percent to about 55 weight percent vinyl acetate monomer and about 0 percent to about 5 percent plasticizer by weight plasticizer.

24. An ion selective electrode construction in accordance with claim 23, wherein said polymer is substantially devoid of plasticizer.

25. An ion selective membrane in accordance with claim 22, wherein said membrane comprises from about 0.1 percent to about 10 percent of said ion selective material by weight.

26. An ion selective electrode construction in accordance with claim 22, further comprising:

polyvinyl chloride polymer combined with said ethylene vinyl acetate polymer, wherein said membrane comprises from about 0.1 percent to about 50 percent by weight said polyvinyl chloride polymer.

* * * * *